United States Patent [19]

Ewing et al.

[11] Patent Number: 4,939,908
[45] Date of Patent: * Jul. 10, 1990

[54] APPARATUS FOR ADJUSTABLY CONTROLLING THE SIZE OF AN ICE BANK

[76] Inventors: Leonard G. Ewing, 2305 Brittany Grace, New Braunfels, Tex. 78130; Milton L. Chesnut, 1404 Deer Run, San Antonio, Tex. 78232

[*] Notice: The portion of the term of this patent subsequent to Apr. 25, 2006 has been disclaimed.

[21] Appl. No.: 272,120

[22] Filed: Nov. 14, 1988

Related U.S. Application Data

[63] Continuation-in-part of Ser. No. 51,080, May 15, 1987, Pat. No. 4,823,556.

[51] Int. Cl.⁵ ................................................ F25C 1/00
[52] U.S. Cl. ........................................ 62/139; 62/201; 62/228.2
[58] Field of Search ................. 62/137, 138, 139, 140, 62/126, 127, 128, 129, 130, 201, 228.2; 137/392

[56] References Cited

U.S. PATENT DOCUMENTS

| | | | |
|---|---|---|---|
| 2,558,063 | 6/1951 | Seyffert | 62/139 X |
| 3,131,335 | 4/1964 | Berglund et al. | 137/392 X |
| 3,496,733 | 2/1970 | Parker et al. | 62/139 |
| 3,502,899 | 3/1970 | Jones | 62/139 X |
| 3,782,130 | 1/1974 | Irvine | 62/128 |
| 4,182,363 | 1/1980 | Fuller | 137/392 |
| 4,823,556 | 4/1989 | Chesnut | 62/139 |

Primary Examiner—Harry B. Tanner
Attorney, Agent, or Firm—Cox & Smith

[57] ABSTRACT

A method and apparatus for adjustably controlling the growth of the solid phase of a substance from around a cooling mechanism, such as the growth of an ice bank around cooling coils, while also minimizing chances of inaccurate control by referencing the apparent resistance of the liquid that is actually in the system rather than a standard value for the same. The invention uses four springs as probes that are positioned relative to one another and are linked with a detachable control circuit in a manner which provides a dead-band in the unit's operation by monitoring the resistance of the liquid at two different distances from the cooling mechanism while the reference resistance is monitored at an even greater distance. A mounting means for the probes advantageously positions the probes relative to cooling coils but allows for adjustment of the size of an ice bank formed around those coils while also protecting the probes and their electrical connections, and a detachable housing for a printed control circuit board is also provided with other advantageous features such as environmental protection.

18 Claims, 4 Drawing Sheets

APPARATUS FOR ADJUSTABLY CONTROLLING THE SIZE OF AN ICE BANK

CROSS REFERENCE TO RELATED PATENT APPLICATIONS

This is a continuation-in-part application of co-pending U.S. application, Ser. No. 051,080, filed May 15, 1987, entitled "ELECTRONIC ICE BANK CONTROL", now U.S. Pat. No. 4,823,556.

TECHNICAL FIELD

The present invention relates to methods and apparatus for sensing the phase transformation of a liquid into a solid and visa versa. More particularly, the invention relates to determining when a solid phase of a material has formed at a location submerged in the material by monitoring the electrical resistance of the liquid, especially in conjunction with apparatus or methods used to control the size of an ice bank in a cooling system that employs cooling coils and utilizes water or other liquid as a heat sink. The present invention also relates to apparatus for housing and detachably connecting an electronic circuit, particularly an electronic ice bank control circuit used to maintain a liquid at a freezing temperature.

BACKGROUND OF THE INVENTION

Cooling systems for cooling beverages or other fluids to a desired temperature typically circulate the beverage through lines (or coils) immersed in water or other liquid which is kept at a freezing temperature. A compressor or other cooling means is employed which circulates refrigerant through cooling coils also immersed in the water or other liquid in order to cause ice formation around the cooling coils. Thus, the liquid phase of the water or other liquid is maintained at the freezing temperature in equilibrium with the solid phase. The frozen liquid around the coils is referred to as an ice bank. As heat is transferred from the beverage to the water or other liquid, the ice surrounding the cooling coils melts. The ice bank thus serves as a heat sink for cooling the beverage. The water remains at a freezing temperature, however, as long there is still sufficient ice present. The heat transferred from the beverage is absorbed as the latent heat of melting, leaving the temperature of the water unchanged. The compressor and circulating refrigerant must, however, cause new ice to be formed in place of the melted ice if the system is to operate continuously. It is therefore necessary to have a closed-loop control system which senses the amount of ice surrounding the cooling coils and actuates the compressor appropriately.

Devices for controlling the size of an ice bank in such cooling systems, ice bank control devices", utilize ice sensing means positioned at a certain distance from the cooling means so that the operation of the cooling means can be controlled relative to that distance. Since the liquid usually crystallizes progressively and radially outward from the cooling coils while the cooling system is cooling the liquid, ice bank control devices therefore allow the ice bank to grow to a predetermined size at which point the cooling cycle of the cooling means is interrupted by the ice bank control device.

Conventional ice bank control devices have generally been of the mechanical type. These devices commonly use a capillary tube containing a solution which freezes when the tube is surrounded by ice. The expanding frozen solution within the capillary tube then compresses a diaphragm which operates an electrical switch. The electrical switch serves to turn a cooling compressor on or off and, thereby, controls the extent of ice formation.

More modern ice bank control devices, however, utilize electronic sensing means to determine the presence of ice. In such devices, electrodes are immersed in the water and current is fed from one electrode to another which is held at ground potential. If a constant current source is used, the potential of the first electrode will be proportional to the resistance of the water or other medium present. Thus, detection of the presence of ice is enabled since the electrical resistance of a liquid changes (usually to a greater resistance) when it undergoes a phase transformation into the solid form. When such a sensing method is combined with a suitable controller, the result is a closed-loop feedback control system which causes the cooling means (typically comprising a compressor) to operate often enough to maintain the water at its freezing point but not so often that excessive ice is formed.

Such electronic ice bank control devices present a number of advantages over their mechanical counterparts including lower cost and greater reliability. Because the electrical resistance of solid phase water is much higher than that of liquid water, such monitoring has enabled fairly accurate determination of the presence of ice. Also, since electronic devices measure the phase change directly rather than indirectly by measuring temperature, their operation is not effected by changes in the freezing point of the water caused by the addition of solids.

Since the cooling means of a system employing such an electronic ice bank control either operates or is shut off, the control scheme is usually referred to as an "on-off" or a "bang-bang" controller. With such systems, the resistance of the water surrounding the cooling coils is compared with a reference value and, if there is a difference, an error signal is produced which causes the compressor to shut off. In the prior art, the reference value is ordinarily a fixed, standard value believed to correspond to that of liquid water.

The resistance of the water used to produce the error signal (hereinafter called "variable resistance") is monitored at a predetermined position a certain distance from the cooling coils. When the value of the variable resistance rises at that position above the reference value, the previous methods indicate that ice has formed at the predetermined position, and this indication initiates the interruption of the cooling process.

A fundamental characteristic of all on-off controllers is oscillation of the controlled variable about the set point. Since the actuator of such a system is operated in an on-off fashion, environmental influences will cause the controlled variable to deviate from the set point when the actuator is off. This produces an error signal to turn the actuator on until the error signal is reduced to zero, and the cycle repeats. Such cycling is normal but is undesirable, if it is too rapid, particularly if the actuator is a mechanical device such as a compressor Rapid start-stop cycles ("fast-cycling") cause excessive wear to the compressor as well as inefficient use of energy. A well known technique of solving this problem is to incorporate a "dead-band" into the controller. A "dead-band" is a range about which the controlled variable is allowed to deviate from the set point before the actuator is either activated or turned off. This is accomplished by making the set point of the system vary between two values according to whether the actuator is on or off. Thus, when the controlled variable is between the higher or lower set points, there is no change in the previously derived error signal which causes the actuator to either remain on or off. Therefore, the range between the higher and lower set points is effectively a "dead-band". In water cooling applications, precise control relative to the controlled variable is not necessary since the only objective of the control scheme is to prevent excessive ice formation around the cooling coils. Incorporating a dead-band into the system, therefore, involves no significant disadvantages.

The most basic of previous similar methods for controlling water cooling involves, simply, measuring the electrical resistance between a single probe and a grounded reference. Circuitry or other means are connected to the probe in order to measure this resistance and compare it with a predetermined fixed value of resistance, which value has been previously determined as a standard for water. A fundamental problem with such a method utilizing a single resistance reading is that there is no means for providing a dead-band. Lack of a dead-band causes the aforementioned practical problems the compressor may undergo rapid start-stop cycles ("fast-cycling") when the progression of ice is immediately adjacent the probe. To solve this problem of fast-cycling, a dead-band must be incorporated into the control system by either mechanical or electronic means.

Another previous method involves monitoring resistance sensors from two probes. The utilization of two probes in this latter method effectively provides for a dead-band. A dead-band is achieved by electronically requiring that both probes sense the ice in order to stop the compressor while also requiring that the ice melt off both probes in order to activate the compressor once again. A predetermined value for the resistance of water has invariably been used as a reference value for this and each other of the previous methods. This previous method involves positioning a first of the two probes nearer the cooling coils so that it will ordinarily sense the progression of ice before the second probe and will sense melting after the second probe. The deadband, therefore, occurs when the first probe senses the ice and when the ice melts from around the second probe. When the system is in this state, the compressor will remain in this previous operating mode, either on or off. If the total volume of the ice pack surrounding the cooling coils is viewed as the controlled variable, this system will cause that variable to oscillate between two set points, represented by ice surrounding the first and both probes, respectively.

Unfortunately, since each of the previous inventions depends on a fixed, predetermined value for the resistance of liquid water, the resulting indications are not always accurate since extraneous and nonstandard factors affect the resistance readings within any tank of water, particularly after extended usage. Most basically, the resistance of water may vary in different geographical locations due to local impurities in the water, which impurities generally raise the resistance of water. Resistance of the liquid water may similarly change within a system over time due to evaporation of the water, which evaporation raises the amount of impurities per volume of water remaining.

Increased resistance of liquid water is also caused by increased amounts of impurities within the system due to accumulation over time. Employment of similar methods also creates problems in systems where the impurity content or the identity of the liquid is purposefully altered; in such situations the reference value must be changed, thus causing delays, particularly when circuitry must be accordingly modified.

Furthermore, deposits on submerged electrical probes, which deposits are natural over time, often affect the resistance measurements. The additional resistance of deposited impurities adds to the resistance which the probe reads, thereby raising the apparent resistance of the water. With the passage of time, coatings of such impurities inevitably adhere to virtually any probe which is submerged in liquid water that is the slightest bit impure. Notably, these coatings tend to be of uniform thickness on surfaces that are subjected to similar environments. Electrolytical plating on the probes may also affect the apparent resistance of the water as recorded by such probes. The electrolytical type deposits have been minimized with some previous methods by utilizing an alternating current rather than a direct current; however, in practice, slight electrolytical plating still occurs with an alternating current. Electrical probes necessary with every employment of the art, therefore, must be periodically replaced or cleaned when incorporated for use with previous inventions.

Therefore, it is a primary object of the present invention to provide an apparatus and method which accounts for resistance variances of water as well as apparent variances in this resistance caused by impurities deposited on the electrical probes, while providing a method for indicating the phase transformation of liquid water to ice.

It is also an object of the present invention to measure the apparent resistance of the liquid. This measured, apparent resistance can be used as a reference rather than some fixed or predetermined value. Changes in the composition of the water will then be automatically compensated for. It is also an object to compensate for changes in the probes themselves. Deposits, electroplating or other factors.

Another object of the present invention is to provide a means for mounting the aforementioned probes for use in an ice bank control system. The mounting of the probes (or "electrodes") must be such that the ground electrode and the reference electrode must always be immersed in liquid water. The two ice sensing electrodes or probes must be mounted so as to define the space in which the ice bank is allowed to grow by the control system.

It is a further object of the present inventions to enable adjustment of the size of the ice bank according to varying operating conditions. For example, if there are to be periods of heavy use, it would be desirable to raise the heat capacity of the heat sink. By increasing the size of the ice bank, the cooling system can handle more throughput of beverage without lowering the temperature of the water bath. Also, different sizes and configurations of the vessel containing the water bath and the associated cooling coils may dictate different optimal sizes of the ice bank. It would be desirable, therefore, for the electrode mounting means to allow a user to adjust the size of the ice bank to suit each individual application.

A related object is to provide detecting means in the form of a plurality of probes with means for mounting onto the coils of a cooling system which forms an ice bank, wherein the mounting means has features which advantageously correlate and provide for adjustment of the positions of the probes.

Another object of the present invention is to provide electrodes and mounting means for use in an ice bank control system of the type described above which render the electrodes relatively resistant to mechanical damage when the cooling coils are lowered into the water bath or removed therefrom. During such operations, there is always the possibility that the electrodes will contact the sides of the water bath vessel or the beverage coils. It is desirable, therefore, to minimize the possibility of breaking or deforming the electrodes as their location is critical to the operation of the ice bank control system. For example, to demonstrate the critically of the probe positions, if the reference electrode were to be broken off or bent during installation of the cooling coils so as to be located closer to the cooling coils than the ice sensing electrodes, the control system would never shut off the compressor and the entire water bath would freeze as a result. The entire cooling system could thereby be completely destroyed.

It is a still further object of the present invention to provide a means allowing the electrodes to be readily replaced with a minimum effort. As aforementioned, electroplating is inevitable in any control system of this type. When the resulting deposits on the electrodes become severe enough to warrant replacement of the electrodes, any time expended during the replacement operation by a repairman is expensive. Also, the time for which the entire system must be shut down may cause expense to a user of the cooling system. It is desirable, therefore, for any electrode mounting means to allow the electrodes to be removed and replaced with a minimum of time and effort.

Furthermore, previous methods have utilized a grounded electrical reference that is dependent on the system in which the previous method is employed. This presents a particular problem where the method is employed in a container or system that is insulated. It is, therefore, another object of the present invention to incorporate the use of a round probe which is independent from the system in which the method is employed.

It is another object of the present inventions to effectively minimize electrolytical plating and coating of electrical probes utilized with the invention.

It is also an object of the present invention to provide an apparatus which utilizes and enables the methods of the present invention.

Another object of the present invention is to provide an apparatus for detecting whether material at a certain location is distinguished from material at a second location, particularly by determining differences in the electrical resistances at the two locations. Yet another object of the present invention is to provide means for detecting the presence or absence of a solid phase in a liquid phase, which means includes protective features for ensuring the desired operation thereof.

Additionally, it is an object of the present invention to provide a method for sensing the presence of a solid phase of any material within a liquid phase of any material, including but not limited to water.

It is another object of the present invention to avoid fast-cycling of apparatus related to any particular employment of the present invention by providing for a dead-band.

Additionally, with the advent of electronic ice bank control devices, there has developed a need for a specialized packaging and connecting apparatus. It is, therefore another object of the present invention to provide a housing for the electronic control circuitry which will serve to protect the electronic components and electrically conductive surfaces from contact with water.

It is a further object of the present inventions to provide a means for easily removing and replacing a printed circuit board upon which the elements of the electronic control circuit are mounted. As all electronic components are destined to fail at some time or other, it is desirable that removal and replacement be accomplished with a minimum of time and effort in order to lower service costs. Much time and effort can be saved by minimizing the number of electrical and mechanical connections which must be severed before the electronic control circuitry can be removed. Accordingly, it is an object of the present invention to provide a connecting means for the printed circuit board containing the electronic circuitry which allows the removal of the printed circuit board without affecting power or sensor connections.

It is still a further object of the present invention to provide a means integral to the housing which allows the state of the final control output of the electronic circuitry to be observed. The final control output is invariably a contact closure, and it is desirable for the state of the contact to be observable without removing the housing or using a voltmeter at the output terminals. For example, when servicing the entire cooling apparatus, it is necessary to determine if the electronic control circuitry is operating properly independent of the operation of the compressor.

SUMMARY DISCLOSURE OF THE INVENTION

Many of the features disclosed and/or incorporated in the present invention are also disclosed in co-pending U.S. patent application, Ser. No. 051,080, filed May 15, 1987 now issued as U.S. Pat. No. 4,823,556, and in co-pending U.S. patent application, Ser. No. 124,157, filed Nov. 23, 1987, now U.S. Patenet No. 4,811,168.

The present invention includes and provides an apparatus for monitoring the electrical resistance of a material and comparing the value of that resistance with a reference value for determining the presence of a solid phase within a liquid. The present invention also involves and provides for continuously monitoring the apparent resistance of the liquid and using this monitored value as a reference rather than using a predetermined fixed value. The effect of resistance variances in different geographical locations and with the passage of time are, thus, cancelled since the variable resistance measured by the controlling probe and the reference resistance measured by the reference probe are dependent on the same liquid. This continuously monitored reference also cancels the effects of probe plating and coating since such effects will be virtually uniform on each of the probes and since the elevated apparent resistance monitored by a controlling probe with deposits thereon will be compensated by an elevated apparent resistance monitored by the reference probe with similar deposits.

As employed in an ice bank control apparatus or other feedback system controlled relative to the formation of ice, the present invention provides for alleviating fast-cycling by incorporating provisions for a deadband. Two controlling probes are positioned so that the second controlling probe is beside the first controlling probe but at a greater effective distance from the cooling coils. Upon sensing ice by both the first and second probes (indicated by increased resistance to ground) the apparatus turns off the cooling means. Visa versa, the sensing of liquid water by both the first and second probes (indicated by the same resistance to ground as from the reference probe) causes the cooling means to turn on. Furthermore, the present invention provides for utilization of a ground probe that is independent from the container or other part of the system that contains the liquid which the method is employed to monitor. The present invention also utilizes an alternating current rather than a direct current in order to minimize the electrolytical plating effects caused by direct current.

Other devices for enabling and utilizing the methods of the present invention are also provided. Such apparatus comprise four electrical probes for measuring the reference resistance and two variable resistances as well as providing a common ground. Circuitry is also included for effecting the indications and controls of the present invention.

The apparatus of the present invention may also comprise a mounting means for mounting the electrical probes (or "electrodes") to a portion of cooling coils. The apparatus also comprises structures for mounting the electrodes and the cables to which the electrodes are connected. The electrodes are metal springs which comprise the current carrying surfaces. The springs are mounted in a single electrode mounting block. In the preferred embodiment, a total of four electrodes are used with two of them being ice sensing electrodes, one being the reference electrode, and the other being the ground electrode. The probe mounting means is designed to be mounted to a portion of the cooling coils around which the ice bank grows. Therefore, the reference electrode and the ground electrode must be located at a greater distance from the cooling coils than either of the two ice sensing electrodes. Since the two ice sensing electrodes define the radii about the coils to which the ice bank is allowed to grow by the control system, the reference and ground electrodes will always be immersed in liquid water. In the preferred embodiment, the appropriate spacing of the electrodes is accomplished by the shape of the electrode mounting block so that springs of the same length may be used for all four electrodes. The orientation of the electrode mounting block is such that when the probe mounting means is mounted on a portion of the cooling coil, the springs are pointed in a direction perpendicular to the length of the cooling coil. The electrode mounting block is of a stair step shape so that the two springs used as the reference and ground electrodes will be at a greater distance from the cooling coils than the other two springs. Also, because of the stairstep shape of the mounting block, the springs used as ice sensing electrodes are located at different distances from the cooling coils to provide the dead-band function described above.

The electrode mounting block is mounted on a cable housing in such a manner as to allow cables to be connected to the springs in a water-tight compartment. The ends of the springs and the cables are connected with standard quick disconnects. The electrode mounting block (also referred to as a "probe cartridge") fits on the cable housing so as to provide a water-tight seal. The inside of the cable housing is filled with epoxy or similar material so that the cables may exit the other side of the cable housing without compromising the integrity of the water-tight compartment where the springs and cables are connected.

The cable housing is slidably mounted in a slot formed by the truss members of the probe mounting means. The probe mounting means provides means enabling it to be mounted on a portion of the cooling coils. By slidably mounting the cable housing in the slot of the probe mounting means, the distance of the four electrodes from the cooling coils may thereby be adjusted. An adjustment member which releasably engages the probe cartridge is provided to lock the probe cartridge in place.

The apparatus of the present invention n!ay also comprise two housings for containing circuitry and otter features of the invention and for operably connecting the same to other components. The first housing particularly houses the electronic printed circuit board, while the second houses terminals and connections for power and sensor cables. The circuit board housing is designed to be fitted on top of the terminal housing and secured by a single screw. In this position, flat pins attached to the printed circuit board are inserted into specially designed slots of the terminal housing which provides the electrical connection between the printed circuit board and the cable terminations. The apparatus provides a unique means for connecting the flat pins to the terminals which provides both a secure mechanical connection as well as a low resistance electrical connection.

Cables enter the terminal housing through slots. Each cable is bent into an S-shape by ridges in the terminal housing before attaching to a screw-type terminal. The bending of the cable by the ridges helps to prevent the cable from being inadvertently pulled loose from its terminal connection.

When the circuit board housing is mounted atop the terminal housing, the terminal housing is partially fit into the circuit board housing. In the preferred embodiment of the present invention, where it is used to house the electronic control circuitry of an ice bank cooling system, this feature prevents accidental splashes of water from reaching the flat pins of the printed circuit board or the cable terminals.

On the top of the circuit board housing is a small, circular lens which receives and concentrates light from a light-emitting element of the printed circuit board. In the preferred embodiment of the present invention, a lamp is mounted on the printed circuit board and electrically connected in series with the contacts controlling the operation of the compressor. This feature enables a user of the present invention to monitor the state of the contacts, and, hence, the operation of the control circuitry, by observing the state of the lamp through the lens mounted atop the circuit board housing. Thus, the operation of the control circuitry may be monitored independently from the operation of the compressor without disconnecting the printed circuit board.

These and other objects, features and advantages of the invention will become evident in light of the following detailed description, viewed in conjunction with the attached drawings of the preferred embodiments. The foregoing and following description of the invention is for exemplary purposes only, though, and the true spirit and scope of the invention is set forth in the appended claims.

DETAILED DESCRIPTION OF THE PREFERRED EMBODIMENTS

Figure 1:
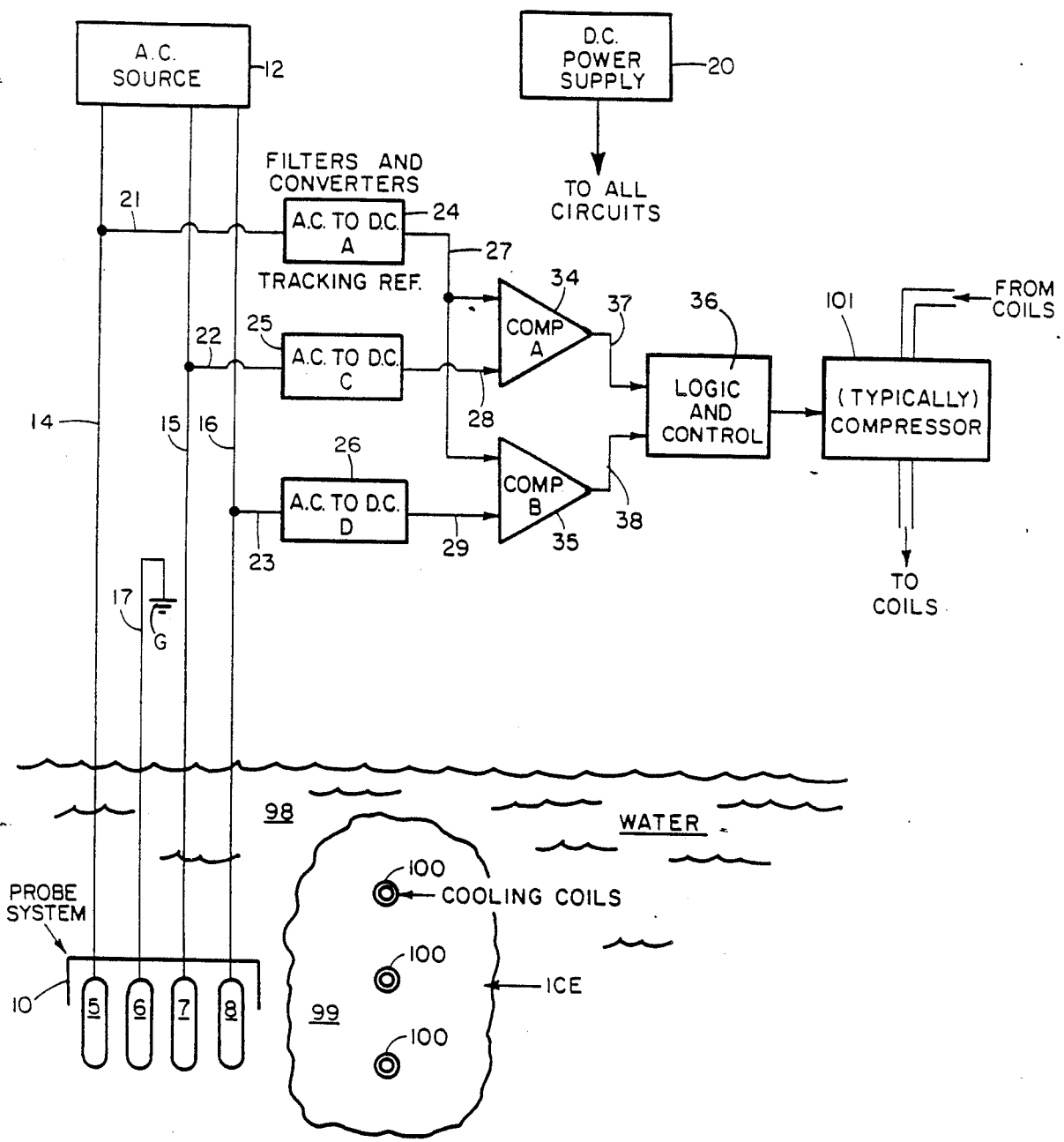
FIG. 1 is a schematic view of the system of the present invention shown relative to an ice bank 99.

Referring to FIG. 1, the apparatus of the present invention, which embodies and utilizes the method of the present invention, is shown in conjunction with compressor 101, which compressor effects the cooling of ice bank 99 with cooling coils 100 when compressor 101 is empowered. Compressor 101 is empowered by DC power supply 20 by means which are discussed further in this application. Compressor 101 and cooling coils 100 are components of a cooling system which contains a bath of liquid water 98. When the compressor 101 is empowered, ice bank 99 grows in size and the perimeters of ice bank 99 progress outwardly from coils 100. When the compressor 101 is not empowered, ice bank 99 melts and the perimeters of ice bank 99 recess inwardly toward coils 100.

Figure 2:
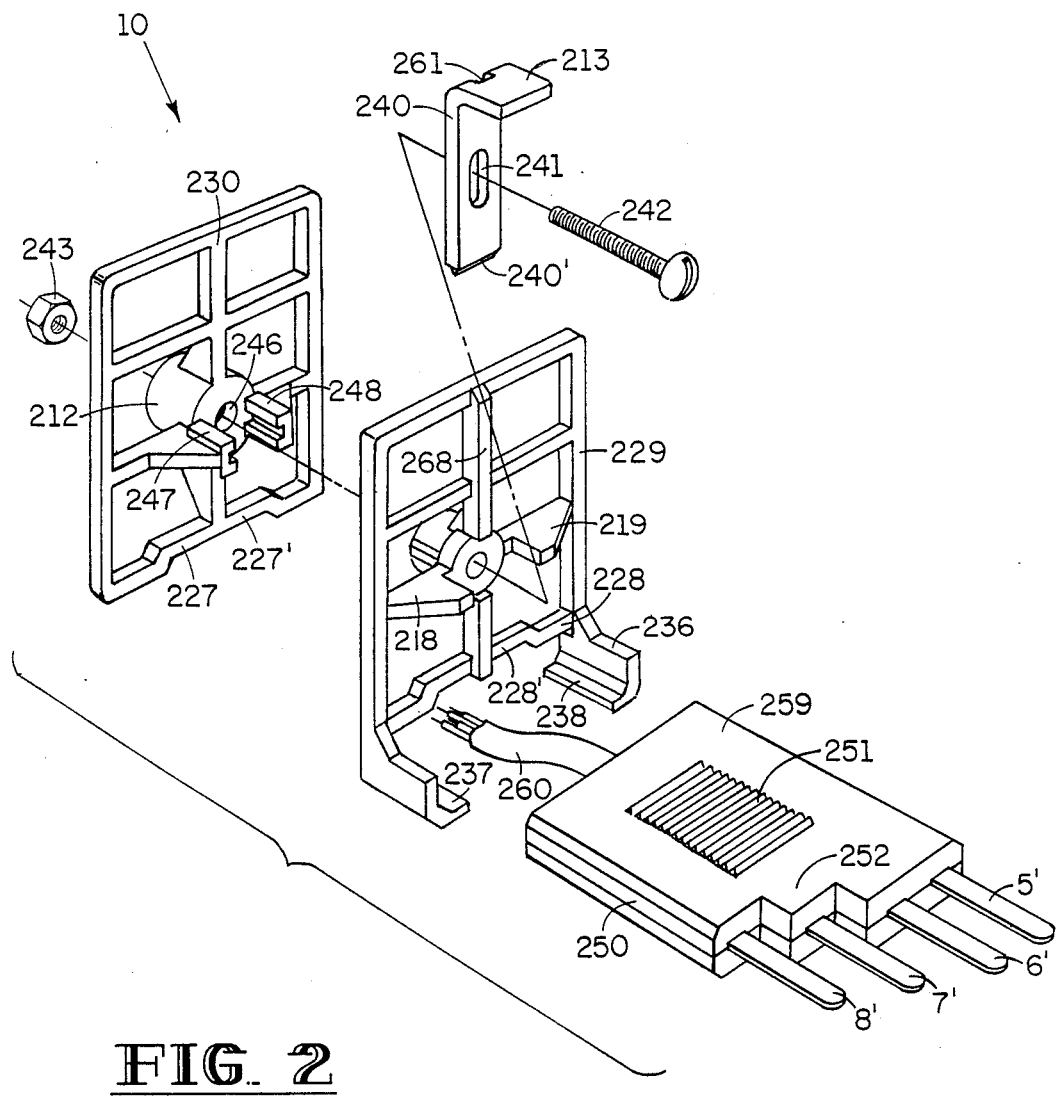
FIG. 2 is an exploded view of the mountable probes of the present invention.
Figure 3:
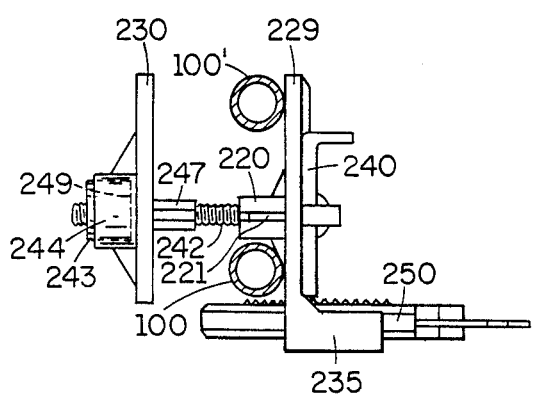
FIG. 3 is a side view of the mountable probes of FIG. 2 shown relative to cooling coils 100 and 100'.
Figure 4:
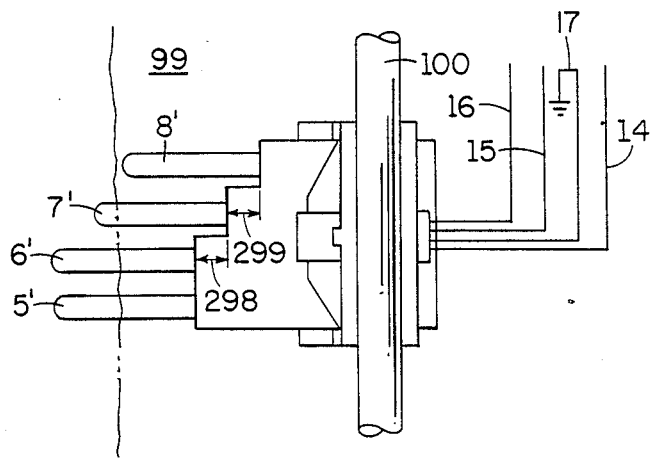
FIG. 4 is a view looking downward on the mountable probes of FIG. 2, which are shown in operative relation with cooling coil 100 and ice bank 99 with the lines 14-17 being shown schematically.

The apparatus of the present invention comprises probes 5-8 positioned in a formation equidistantly spaced (as shown in FIG. 1 and as in the embodiment of FIGS. 2-4). The compositions and dimensions of probes 5 through 8 are similar to one another. Probes 5, 7 and 8 are in electrical communication with the control circuitry of the present invention through lines 14-16, respectively. Probe mounting means 10, composed of an electrically insulative material, is rigidly connected to probes 5 through 8 for fixing the respective positioning of said probes 5 through 8 relative to one another and to ice bank 99. The preferred embodiment of probes 5-8 and probe mounting means 10 is discussed in more detail in relation to FIGS. 2-4. Each of probes 5, 7 and 8 are also in electrical communication with an alternating current source, 12 which is a means for producing alternating current; this operative connection with the alternating current source 12 is for providing alternating current to probes 5, 7 and 8. Probe is a ground probe and is operatively connect in electrical communication with an appropriate ground G. Probe 6 is a common ground for probes 5, 7 and 8. Lines 14, 15 and 16 are insulated conductors are operatively connected between alternating current source 12 and probes 5, 7 and 8, respectively, in a manner which provides alternating current to each of probes 5, 7 and 8. The alternating current in each of lines 14-16 is with the alternating current in each of the other ones of lines 14-16. The peak-to-peak in phase and of equivalent amplitudes of the voltages produced by the alternating current, measured at any point along insulated conductors 14, 15 and 16 are proportional to the resistances between probe 6 and probes 5, 7 and 8 respectively owing to the current amplitude being maintained constant through each insulated conductor.

Converters 24, 25 and 26 are operatively connected in electrical communication with insulated conductors 14, 15 and 16, respectively, by leads 21, 22 and 23, respectively. Each of converters 24, 25 and 26 convert the alternating current to direct current signals, the amplitudes of which are proportional to the peak-to-peak amplitude of the alternating current signals. The rectified alternating current signals are then filtered before inputting to comparators 34 and 35. Converters 24, 25 and 26 are also operatively connected in electrical communication with DC power supply 20 for enabling the alternating current to direct current conversion. DC power supply 20 is further operatively connected to alternating current source 12 for receiving alternating current power from alternating current source 12. DC power supply 20 comprises means for transforming the received alternating current power to direct current power to all circuits of the system which need DC power. DC power supply 20 is a common power supply for converters 24, 25 and 26 as well as logic and control unit 36. Converters 24, 25 and 26 are similar in their electrical characteristics Leads 27, 28 and 29 are operatively connected in electrical communication with converters 24, 25 and 26, respectively, for conducting the direct current signals from said converters 24, 25 and 26, respectively. Comparator 34 is operatively connected to receive the direct current signals from leads 27 and 28 to compare the signals from leads 27 and 28. Comparator 35 is operatively connected to receive the direct current signals from leads 27 and 29 to compare the signals from leads 27 and 29. Comparators 34 and 35 have similar electrical characteristics. The electrical characteristics of each comparator 34 and 35 are such as to produce a high signal when the compared input signals are different and a low signal when the compared input signals are the same. A high output signal from a comparator therefore indicates the presence of ice around the controlling probe 7 or 8 which inputs into it.

Logic and control unit 36 is operatively connected in electrical communication with comparator 34 and 35 through leads 37 and 38, respectively. Comparator 34 provides an electrical comparison signal to logic and control unit 36 through lead 37. Comparator 35 communicates the appropriate electronic comparison signal to logic and control unit 36 and through lead 38.

Logic and control unit 36 comprises appropriate electronic circuitry to analyze the comparison signals that are received through leads 38 and 37. Logic and control unit 36 further includes electronic circuitry for transmitting electrical signals for controlling the operation of the compressor 101. These controlling signals are transmitted through output wires 39. The circuitry of logic and control unit 36 controls the operation of the compressor 101 by means incorporated with logic and control unit 36 for engaging and disengaging the compressor 101 with power from DC power supply 20. Output wires 39 are operatively connected to the circuitry of logic and control unit 36 and are operatively connectable to compressor 101 for enabling electrical communication between logic and control unit 36 and compressor 101.

The circuitry of logic and control unit 36 is such that when both comparators 34 and 35 are producing high signals, corresponding to ice surrounding both probes 8 and 7, the compressor 101 is stopped. When both comparators 34 and 35 produce low signals, corresponding to water surrounding both probes 8 and 7, the compressor is started. Any other combination of outputs from the comparators produce no change in the operating state of the compressor.

In operation, probes 5 through 8 are to be positioned submerged in water or a water based solution, with probe 8 being the closest probe to the origin of ice formation and the likely direction from which ice production will progress. Such a positioning is shown in FIG. 1 as the ice bank 99 will form progressively outwardly from coils 100. Although FIG. 1 displays the present invention employed in a system which contains water, the present invention may also be employed in any system which contains a liquid that transforms into the solid phase, which solid phase has an electrical resistance distinguishable from the electrical resistance of the liquid phase.

Accordingly, when the alternating current is provided by alternating current supply 12 through insulated conductors 14, 15 and 16, current also flows from each of probes 5, 7 and 8 to ground probe 6. The resistance between ground probe 6 and probe 5 is the reference resistance. The resistances between probe 7 and probe 6 and between probe 8 and probe 6 are variable resistances. The substance surrounding probes 5 and 6 is always liquid since, as will be apparent further in this discussion, progression of the bank of the ice bank 99 ceases when the ice bank 99 has surrounded probe 7. The reference resistance, thus, will always correspond to the resistance of the liquid within the system.

The method of the present invention is also schematically represented in FIG. 1. The method of the present invention may utilize an apparatus similar to the apparatus of the present invention. Components of the apparatus of the present invention, thus, are referenced in the description of the preferred method of the present invention. The method involves first selecting positions submerged in the liquid water, which positions are selected to approximate desired volume limits of the ice bank 99. After these predetermined positions are selected, the probes 7 and 8 are situated at the predetermined position with probe 8 positioned nearer the cooling coils 100 than the other probe 7. Probes 6 and 5 are then located at some greater distance from the cooling coils 100. Insulated conductor 17 is connected in electrical communication with an electrically grounded object. Once probes 5-8 are positioned, alternating current source 12 and direct current power supply 20 are operated to empower the electrical circuitry of the apparatus of the present invention. This empowering of the electrical circuitry enables the operation of the apparatus of the present invention.

Thus, as the perimeter of ice bank 99 progresses, probe 8 is the first of probes 5-8 to be surrounded by ice bank 99. As the perimeter of the ice bank 99 progresses further, probe 7 is surrounded by ice and the resistance between it and ground probe 6 rises above the reference resistance; each of comparators 34 and 35 therefore transmit a high signal to logic and control unit 36. Sensing that both comparators have gone high, logic and control unit 36 transmits an electrical signal for interrupting the cooling operation of the compressor 101. The cooling operation of the system is, thus, ceased and ice bank 99 ceases to grow in size. Once the operation of the compressor is interrupted, ice bank 99, accordingly, begins melting. After ice bank 99 has melted from around probe 8, logic and control unit 36 senses that the resistance between it and ground probe 6 is equal to the reference resistance, and logic and control unit 36, accordingly, transmits an electrical signal to compressor 101 for reinitiating the operation of compressor 101. Ice bank 99, subsequently, ceases melting and the bank of ice bank 99 again progresses toward probe 7. The operation of the system may be continued in this manner indefinitely to effectively control the size of ice bank 99. Thus, the operation of the apparatus of the present invention in conjunction with compressor 101 and cooling coils 100 enables, embodies and utilizes the method of the present invention in a preferred manner.

The method of the present invention, basically, includes the steps of: selecting a position within the liquid water, which position is desired by the implementer of the method of the present invention to be the approximate limit of the progression of a perimeter of ice bank 99; empowering the circuitry of the apparatus of the present invention with currents from alternating current source 12 and direct current power supply 20; with that circuitry, representing the reference resistance as an electrical signal and transmitting that signal through lead 21; similarly representing the variable resistances as electrical signals transmitted through lead 22 and lead 23; to converters 25 and 26, respectively; filtering each of the electronic signals transmitted through leads 21, 22 and 23 to minimize undesirable electronic characteristics of the signal; converting the electrical signals from leads 21, 22 and 23 to direct current signals with converters 24, 25 and 26, respectively; transmitting those direct current signals from converters 24, 25 and 26 through leads 27, 28 and 29, respectively, to comparators 34 and 35; comparing and determining the electronic differences between the direct current signal in lead 28 with the direct current signal in lead 27, which comparison is enabled by comparator 34; comparing and determining the electronic differences between the direct current signal transmitted through lead 29 with the direct current signal transmitted through lead 27, which comparison is enabled by comparator 35; representing the respective differences determined by comparators 34 and 35 as electronic signals and transmitting these signals through leads 37 and 38, respectively, to logic and control unit 36; utilizing logic and control unit 36 to determine, from the electronic signals transmitted through leads 37 and 38, the desired operation of compressor 101 for melting and cooling ice bank 99; and controlling the operation of compressor 101 according to the determinations of logic and control unit 36.

More specifically, the method of determining and controlling the operation of compressor 101 by logic and control unit 36 involves several steps. For demonstration purposes, these steps begin at the initial start-up of compressor 101; however, the method of the present invention may be employed at any stage during the production of ice bank 99. The steps of this determination and control of compressor 101 by logic and control unit 36 basically comprise engaging compressor 101 with power from DC power supply 20 to initiate operation of compressor 101 and to initiate formation of ice bank 99; determining from the electronic signal transmitted through lead 37 when the resistance between probes 7 and 6 is greater than the reference resistance and, when such occurs, interrupting the power supply from DC power supply 20 to compressor 101 to stop the operation of compressor 101 and begin melting ice bank 99; determining from the electronic signal transmitted through lead 38 when the resistance of the material between probes 8 and 6 is equal to the reference resistance and, when such occurs, reengaging compressor 101 with power from power supply 20 for reinitiating growth of ice bank 99; and continuing the previous steps. By this method, the melting and reinitiating of the growth of ice bank 99 may be continued for as enduring a period of time as is desired by the implementor of the method of the present invention.

Referring to FIG. 2, there is shown an exploded view of a probe mounting means 10' and a probe cartridge 250 having probes 5'-8', the combination of which is collectively referred to as the "mountable probes", of the present invention. The mountable probes, which are also shown in FIGS. 3 and 4, comprise features which function as the probe mounting means 10 and probes 5-8 represented in FIG. 1, except that the relative positioning of the probes of the mountable probes is fixed by the physical characteristics of probe cartridge 250 according to a predetermined, desired relationship. Springs 5'-8' of the mountable probes function as the probes 5-8, respectively, of FIG. 1 in combination with means for operatively positioning and adjusting the position thereof relative to cooling coils 100 of FIG. 1. For relating the mountable probes of FIGS. 2-4 with the probe system of FIG. 1 and the operation of the electrical circuitry of FIG. 1, springs 5'-8' are numbered in correlation with the probes 5-8 of FIG. 1 and any references to probes 5-8 similarly reference and descriptive of springs 5'-8', respectively.

Probe mounting means 10', functioning in part as the probe mounting means 10 of FIG. 1, basically comprises truss members 229 and 230, adjustment member 240, mounting bolt 242 and nut 243. As is evident from FIG. 2, the shaft of mounting bolt 242 is received in linear succession through: slot 241 in adjustment member 240, hole 245 in truss member 229, hole 246 in truss member 230, and is then threadably received through nut 243. Thus, mounting bolt 242 is positioned in its operative position for mounting probes 5-8 relative to cooling coil 100 and an ice bank 99 formed about cooling coil 100. Truss members 229 and 230 each have various cross members including lower member 228 and central member 268, for reinforcing their structure and for engaging a cooling coil therebetween, as well as other features. Each of truss members 229 and 230 has a cylindrical protrusion 211, 212, respectively, surrounding a hole 245, 246, respectively, near its center. Cylindrical protrusions 211 and 212 are for reinforcing the connection of mounting bolt 242 through holes 245 and 246, respectively. Cylindrical protrusion 211 has two ridge-like keys 221 (only one of which is shown) protruding radially from opposite sides thereof. As is evident in FIG. 3, the longitudinal dimension of ridge-like keys 221 is parallel to mounting bolt 242. Cylindrical protrusion 212 has a central recess 249 (shown in hidden line in FIG. 3) having a size and shape which corresponds with the size and shape of nut 243 for receiving nut 243 therein and opposing the rotation of nut 243 about the central access of mounting bolt 242.

When mounting bolt 242 is positioned in its operative position, mounting bolt 242 is threadably tightened into nut 243 in order to draw truss members 229 and 230 toward one another, thereby clamping probe mounting means 10 onto a cooling coil 100 positioned between truss members 229 and 230. When truss members 229 and 230 are drawn towards each other as described, grooved receiving members 247 and 248, which each have a central inwardly-facing groove aligned with the central axis of mounting bolt 242, mate with and slidably receive keys 221. Thus, grooved receiving members 247 and 248 function to slidably receive and align the cylindrical protrusion 220 of truss member 229, thereby ensuring that truss members 229 and 230 are parallel and that the orientations of their shapes correspond to one another. Thus, keys 221 and grooved receiving members 247 and 248 provide means preventing rotation of truss member 230 relative to truss member 229.

Receiving arms 235 and 236 are integral with and extend from the lower portion of truss member 229 away from truss member 230. Receiving arms 235 and 236 have flanges 237 and 238, respectively, for slidably receiving and supporting probe cartridge 250. Lower member 228 of truss member 229 is substantially straight but has a raised portion 228' in its central region, which raised portion 228 is an adaptation enabling reception of a series of ridges 251 of probe cartridge 250. Probe cartridge 250 has a frontal profile which corresponds with the internal shapes of receiving arms 237, 238 and lower member 228. Therefore, the combination of the features of lower truss 228 and receiving arms 235, 236 form a slot which slidably and snugly receives probe cartridge 250 therebetween. The lower member 227 of rear truss member 230 also has a central raised portion which corresponds with the central raised portion 228' of lower truss 228 for receiving ridges 251 of probe cartridge 250. The series of ridges 251 on probe cartridge 250 are respectively parallel to one another, are perpendicular to springs 5'-8' and are parallel to the plane of truss member 229. The mating of probe cartridge 250 between receiving arms 235, 236, lower member 228 and lower member 227 enables a snug but slidable fitting of probe cartridge 250 therebetween.

Adjustment member 240 is basically a longitudinal member having a bevelled tip 240' at its lower end for engaging ridges 251. Because bevelled tip 240' is parallel to ridges 251, bevelled tip 240' fits between adjacent ones of ridges 251 and prevents further sliding movement of probe cartridge 250 when adjustment member 240 is fixed in engagement with ridges 251. The upper end 213 of adjustment member 240 extends perpendicularly from the rest of adjustment member 240 to provide a handle by which adjustment member 240 can be gripped for manually raising and lowering adjustment member 240. Mounting bolt 242, received through slot 241, secures and fixes the elevation of adjustment member 240 relative to truss member 229 and probe cartridge 250 when mounting bolt 242 is fully tightened within nut 243. The vertical movement of adjustment member 240 is limited by the dimensions of slot 241. By loosening mounting bolt 242, movement of truss members 229 and 230 relative to one another is enabled and adjustment member 240 is loosened. Thus, due to the loosening of adjustment member 240, manual adjustment of the elevation of adjustment member 240 is enabled.

Fins 218 and 219, which are integral with and protrude from truss member 229 function as guides for the sliding movement of adjustment member 240 when mounting bolt 242 is loosened. Fins 218 and 219 guide such sliding movement of adjustment member 240 so that the longitudinal axis of adjustment member 240 remains perpendicular to the upper surface 259 of probe cartridge 250. Additionally, adjustment member 240 has a central groove 261 along its length for further guiding the sliding movement of adjustment member 240 in a direction perpendicular to the upper surface 259 of probe cartridge 250. Central member 268 of truss member 229 is of greater thickness than other members of truss member 229. Central member 268 is, thus, raised relative to other members of truss member 229 so that central member 268 provides and elongate guide for mating with groove 261 of adjustment member 240.

Thus, when mounting bolt 242 is loosened, adjustment member 240 can be manually raised so that its bevelled tip 240' disengages the ridges 251 of probe cartridge 250 to enable sliding movement of probe cartridge 250 within receiving arms 235 and 236 in a direction perpendicular to the plane of truss member 229. Then, when probe cartridge 250 has been appropriately adjusted according to the desired size of an ice bank relative to the position of truss member 229, adjustment member 240 is again lowered so that bevelled tip 240' reengages ridges 251. Thus, the distance of the probes 5'-8' from truss member 229 and likewise from a cooling coil 100 on which probe mounting means 10' is clamped, can be adjusted to a plurality of distances, each of which correspond to the engaging of bevelled tip 240' in respectively different troughs between adjacent ones of the series of ridges 251.

Probe cartridge 250 has springs 5'-8' protruding from its distal end 252. Springs 5'-8' are cantilevered flat springs but, in an alternative embodiment (not shown) springs 5'-8' are helical springs, which inherently enable greater freedom of flexibility than the flat springs 5-8' of the preferred embodiment. The cantilevered flat springs which are springs 5'-8' in the preferred embodiment, however, are preferred though because of their simple, flat shapes which enable assembly of probe cartridge 250 with a water-tight seal that prevents leakage of water to the space within probe cartridge 250 through the connections of probes 5'-8' therewith. Probe cartridge 250 is formed of two halves, 253 and 254, which are sealed together around cable 260 and probes 5'-8' to form a water-tight enclosure within probe cartridge 250. Each of springs 5'-8' are connected to an insulated electrical lead within the water-tight enclosure of probe cartridge 250 in a manner which enables operative electrical communications between springs 5'-8' and the circuitry shown in FIG. 1. Thus, referring to FIG. 4, spring 5' is electrically connected to line 14 as is probe 5 in FIG. 1; spring 6' is electrically connected to line 17 as is probe 6 in FIG. 1; spring 7' is electrically connected to line 15 as is probe 7 in FIG. 1; spring 8 is electrically connected to line 16 as is probe 8 in FIG. 1.

Referring to each of FIGS. 2-4, the distal end 252 of probe cartridge 250 has a stairstep form so that spring 7' is located one stairstep further from truss member 229 than spring 8', and springs 5' and 6' are similarly located one stairstep further from truss member 229 than spring 7'. Therefore, when probe mounting means 10' is operatively clamped onto a cooling coil 100 in the manner described, springs 5' and 6' are one stairstep further than spring 7' from cooling coil 100, and spring 7' is one step further than spring 8' from cooling coil 100. Each of the stairstep features of probe cartridge 250 are equally proportioned so that the dimensions 298 and 299 shown in FIG. 4 are equivalent. Each of springs 5'-8' protrude an equal distance from probe cartridge 250. Springs 5' and 6' can thus function as the reference and ground probes 5 and 6, respectively as described in relation to FIG. 1. Springs 7' and 8', on the other hand, function as the ice sensing probes 7 and 8 which define the sides of the ice bank and enable the dead-band characteristic of the ice bank control system.

Although not shown, springs 5'-8' are connected to lines 14, 17, 15 and 16, respectively, by means of quick disconnects which are each integral with the respective end of the respective electrical line 14, 17, 15, 16. Each of said quick disconnects is a female member of the type commonly available for electronically connecting with spade-like male members having the width of one of springs 5'-8'. Thus, each of said quick disconnects is adapted to slidably release one of springs 5'-8' therefrom in the direction of that spring's longitudinal dimension when appropriate force is exerted on the respective spring. When cartridge 250 is being sealed to enclose the respective connections of springs 5'-8' with the lines of cable 260, the enclosure therein is filled with an epoxy or a similar non-conductive material. Each of the electrical lines to probes 5'-8' are individually insulated and are collected to comprise cable 260. Thus, in the event that one of the springs 5'-8' is desired to be replaced, its seal with probe cartridge 250 can be broken and the spring slidably released from the quick disconnect so that a replacement spring can be inserted in place of the removed spring. After a spring 5'-8' has been so replaced, the seal between that spring and probe cartridge 250 is resealed.

Although shown in FIG. 2 as having the springs 5'-8' protruding in a direction opposite truss member 230, the direction of protrusion of springs 5'-8' relative to cooling coils 100 is reversible. Because the profile features of probe cartridge 250 are laterally symmetrical, probe cartridge 250 may be turned around to protrude springs 5'-8' in the opposite direction. Alternatively, to accomplish the same result by another means, the mounting bolt 242 of probe mounting means 10' can be loosened or removed in order to enable complete repositioning of probe mounting means 10' so that springs 5-'8' protrude in an opposite direction from cooling coil 100.

As is evident from FIG. 3, when probe mounting means 10' is mounted on cooling coils 100 and 100, the probe mounting means 10' not only clamps cooling coils 100 and 100 between truss members 229 and 230, but also enables positioning of probe cartridge 250 in a position such that cooling coil 100 is completely surrounded by the combination of probe mounting means 10' and probe cartridge 250. The relative proportions of probe mounting means 10' are such that when cooling coil 100 is standardly sized as in standard beverage dispensing means, cooling coil 100 fits between truss members 229 and 230 and also between probe cartridge 250 and cylindrical protrusion 220. Additionally, if cooling coil 100' is standardly spaced relative to cooling coil 100, truss members 229 and 230 are of sufficient dimensions to clamp cooling coil 100' therebetween. Such clamping on both of two adjacent cooling coils 100 and 100' insures the ideal perpendicular protrusion of springs 5'-8' from a plane common to the two cooling coils 100 and 100'. Thus, since the perimeter of an ice bank around adjacent cooling coils typically forms parallel to such a plane, springs 5'-8' are ensured to protrude perpendicularly through the perimeter of ice bank 99. In any event, probe mounting means 10' is structured to mount on a single cooling coil in either of the positions of cooling coils 100 and 100 shown in FIG. 3.

Figure 5:
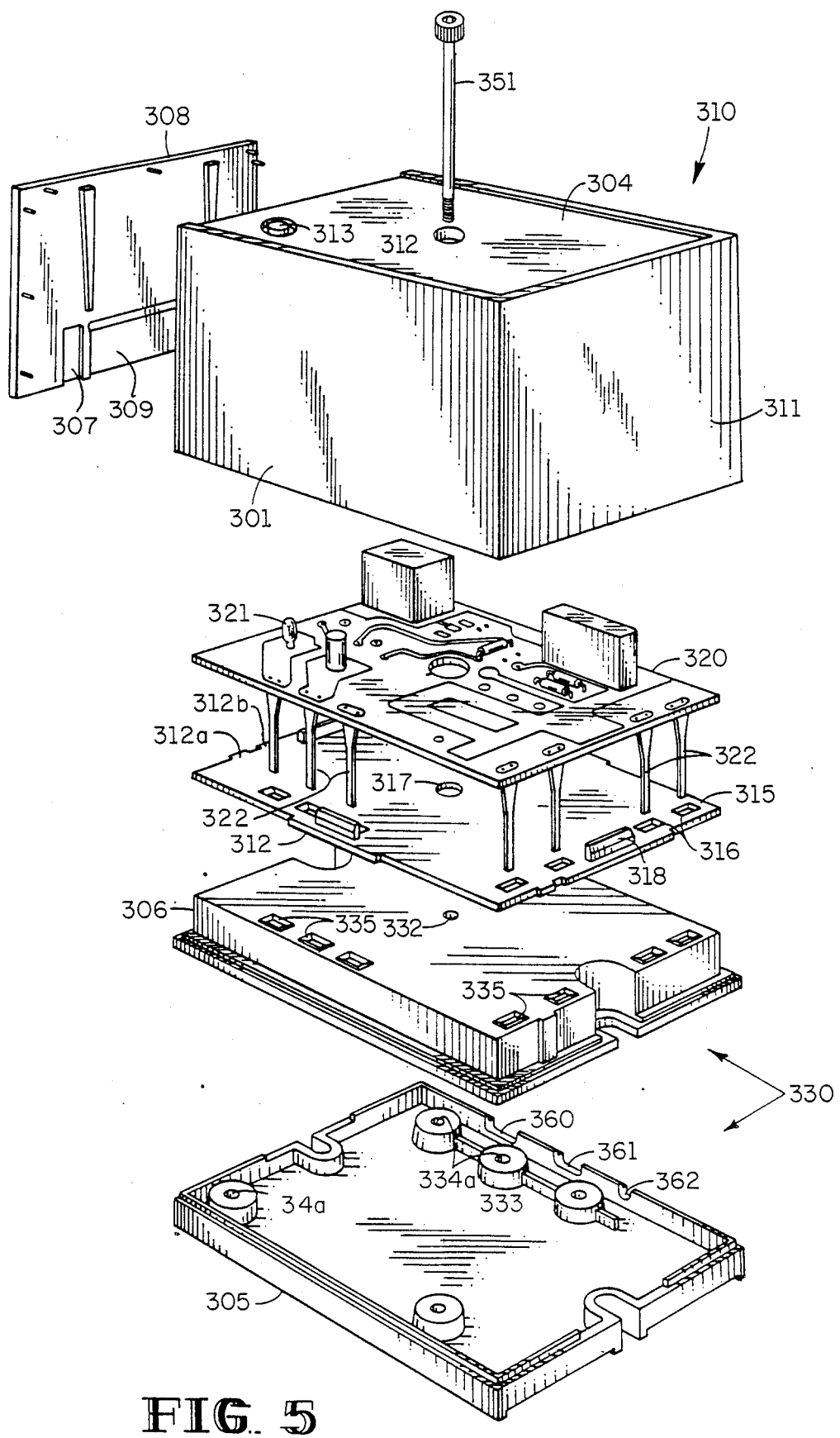
FIG. 5 is an exploded view of the circuit board housing and connecting means of the present invention.
Figure 6:
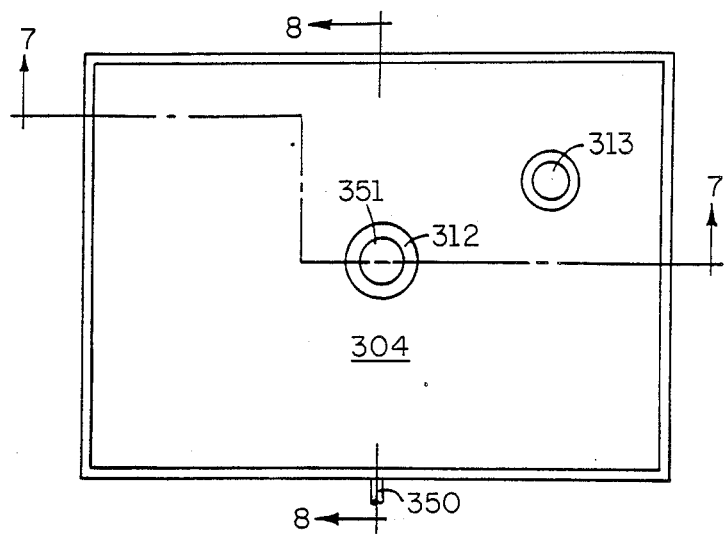
FIG. 6 is a view looking downward on the top planar member of the circuit board housing and connecting means of FIG. 5, showing sectional lines which correspond to FIG. 7 and FIG. 8.

Referring to FIG. 5, there is shown circuitry housing 300 for housing the control circuitry schematically shown in FIG. 1 and for detachably connecting those portions in an ice bank control system. Circuitry housing 300 is a generally rectangular enclosure comprising a cover 311, end member 308, and base plate 305. Upper portion 306 is interposed within circuitry housing 300 and subdivides circuitry housing 300 into two enclosures—circuit board housing 310 and terminal housing 330. Even though upper portion 306 functions in conjuction with both of those enclosures, further references to circuit board housing 310 refers to the combination of cover 311 and end member 308, and further reference to terminal housing 330 refers to the combination of base plate 305 and upper portion 306. Cover 311 is an integration of four planar members 301–304, members 301–303 being side members 301–303, and member 304 being a top member 304.

Printed circuit board 320 is mounted atop circuit board support plate 315. Printed circuit board 320 is electronically connected to power and sensor cable terminations by means of flat pins 322. Flat pins 322 insert into slots 316 of circuit board support plate 315. Various tabs 312 protruding from the edges of circuit board support plate 315 insert into corresponding notches of circuit board housing 310 when circuit board support plate 315 is inserted into circuit board housing 310; for instance, tabs 312a and 312b insert into notches 307 and 309, respectively. An outwardly facing pawl 318 is integral with circuit board support plate 315 at the center of each edge thereof. The pawls 318 are engaged within grooves on the interior of cover 311 and end member 308 when circuit board support plate 315 is inserted into circuit board housing 310; for instance, pawl 318a engages groove 314 on the interior of end member 308. End member 308 of circuit board housing 310 is held to the rest of the housing my means of tacks or adhesive. End of member 308 is, thus, removable which enables insertion of circuit board support plate 315 and printed circuit board 320.

Figure 8:
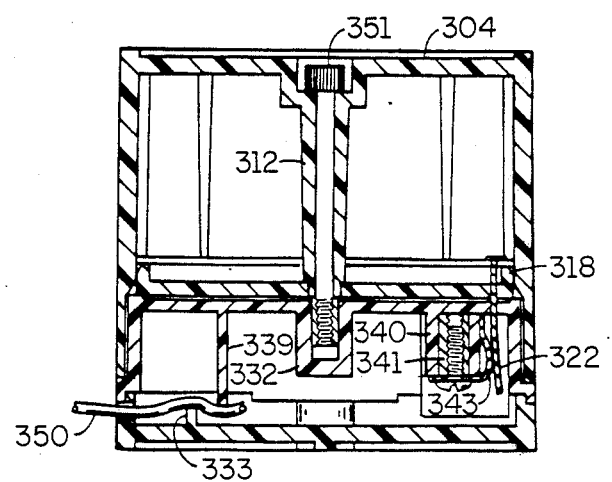
FIG. 8 is a cross-section of the apparatus along the sectional line labeled 8—8 in FIG. 6.

Terminal housing 330 comprises an upper portion 306 and base plate 305. When upper portion 306 and base plate 305 are fitted together, a housing is formed which receives cables 350 through cable slots 360, 361, and 362. Three cable slots are shown in this preferred embodiment for receiving a power in, power out, and a single sensor cable. The wires of cables 350 attach to ribbon conductors 343 by means of terminal screws 341. As shown in FIG. 8, cable 350 is bent into an S-shape by ridge 333 of base plate 305 and ridge 339 of upper portion 306. This helps to prevent cable 350 from being inadvertently pulled loose from terminal screws 341.

Figure 7:
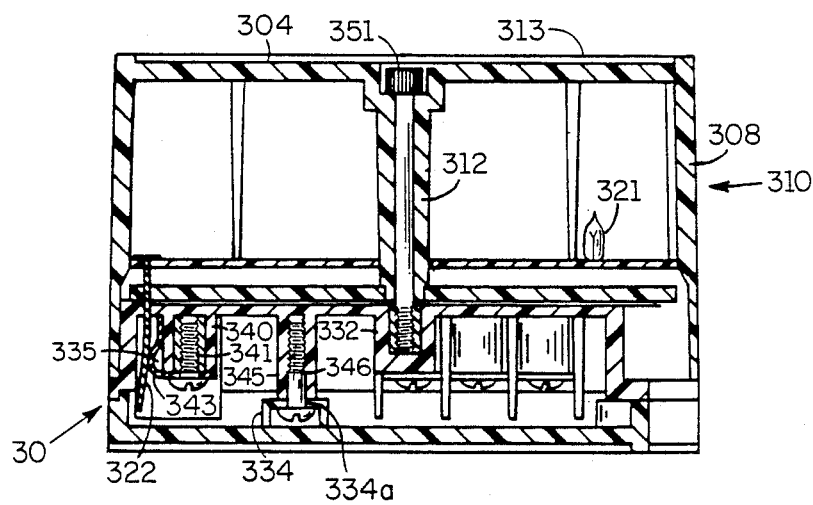
FIG. 7 is a cross-section of the apparatus along the sectional line labelled 7—7 in FIG. 6.

For each flat pin 322 of printed circuit bard 320, there is a corresponding ribbon conductor 343, terminal screw 341, and terminal screw post 340. Terminal screws 341 are threadably engaged in terminal screw posts 340 of upper portion 306 as shown in FIG. 7 and FIG. 8. For each terminal screw post 340 in upper portion 306, there is a slot 335 located adjacently. As shown in FIG. 7 and FIG. 8, ribbon conductors 343 are located within each slot 335 and have an extension connected to each terminal screw post 340. A hole through the extension of each ribbon conductor 343 allows passage of the respective terminal screws 341 as it secures a wire of one of cables 350 to ribbon conductors 343 and terminal screw post 340. As each flat pin 322 is inserted into its respective slot 335, the ribbon conductor 343 is deformed so as to exert a holding force against the flat pin 322. The deformation of ribbon conductor 343 is such that it becomes slightly flattened which results in a large area of electrical contact between pin 322 and ribbon conductor 343.

A plurality of holding screws 346 secures base plate 305 to upper portion 306. Holding screws 346 are inserted through holes 334a located within cup-like depressions 334 in base plate 305 as shown in FIG. 7. When upper portion 306 is mounted atop base plate 305' cup-like depression 334 is positioned flush against holding screw post 345 of upper portion 306. As shown in FIG. 7, holding screws 346 threadably engage holding screw posts 345.

After printed circuit board 320 and circuit board support plate 315 are mounted within circuit board housing 310, circuit board housing 310 is mounted atop terminal housing 330. Flat pins 322 of printed circuit board 320 engage slots 335 of terminal housing 330. Thus, in the completely assembled portion, printed circuit board 320 is electrically connected to the appropriate terminals in terminal housing 330. Circuit board housing 310 is secured to terminal housing 330 by means of a single screw 351 which threadably engages a hole 332 in upper portion 306 as shown in FIG. 5. Screw 351 inserts into screw post 312 of top planar member 304 of circuit board housing 310. Screw post 312 passes successively through hole 323 in printed circuit bard 320, and hole 317 in circuit board support plate 315. Thus, by removing a single screw, printed circuit board 320 may be disconnected from the rest of the unit without disturbing the cable connections within terminal housing 330.

Also located on top planar member 304 of circuit board housing 310 is a lens 313 as shown in FIG. 5. Lens 313 is aligned with a lamp 321 of printed circuit board 320. The light emitted by lamp 321 is gathered and transmitted by lens 313. Lamp 321 may be installed so as to light when any appropriate status of printed circuit board 320 occurs. In the preferred embodiment, however, lamp 321 is connected in series with the output contacts which serve to turn on the compressor 101, of the ice bank cooling system shown in FIG. 1. Thus, an operator may easily determine whether the circuitry of printed circuit board 320 is operating properly independently of the operation of the compressor 101.

Although the invention has been described in conjunction with the foregoing specific embodiments, many alternatives, variations and modifications will be apparent to those of ordinary skill in the art, especially in light of the background and details of this description including the attached drawings and the appended claims. Those alternatives, variations and modifications are intended to fall within the spirit and scope of the appended claims.

What is claimed is:

1. An apparatus for adjustably controlling the size of an ice bank around a cooling coil immersed in a water bath as part of a refrigeration system comprising:
    a first controlling probe immersed in said water bath located at a distance from said cooling coil representing the minimum desired size of the ice bank;
    a second controlling probe immersed in said water bath and located at a distance from said cooling coil representing the maximum desired size of the ice bank;

a ground probe immersed in said water bath and located at a greater distance from said cooling coil than either of said first or second controlling probes;

a reference probe immersed in said water bath and located at a greater distance from said cooling coil than either of said first or second controlling probes;

means for producing a constant current between said first controlling probe and said ground probe, between said second controlling probe and said ground probe, and between said reference probe and said ground probe.

means for measuring the voltage potentials of said first controlling probe, said second controlling probe, and said reference probe as constant current flows from each of said probes to said ground probe;

means for turning said refrigeration system on when the potential of said first controlling probe is equal to the potential of said reference probe;

means for maintaining the refrigeration system in an on condition even as the potential of said first controlling probe becomes greater than the potential of said reference probe due to ice formation around said first controlling probe and for turning off the refrigeration system when the potential of said second controlling probe becomes greater than the potential of said reference probe due to ice formation around said second controlling probe; and means for adjusting the distance at which said first controlling probe is located from said cooling coil, thereby adjusting the minimum desired size of the ice bank.

2. The apparatus of claim 1 wherein said adjusting means comprises means for enabling slidable movement of said first controlling probe relative to said cooling coil.

3. The apparatus of claim 2 further comprising means for fixing the positions of said first controlling probe, said second controlling probe and said reference probe relative to one another so that the respective distances at which said second controlling probe and said reference probe are located from said cooling coil are adjusted simultaneously with adjustment of the distance at which said first controlling probe is located from said cooling coil.

4. The apparatus of claim 1 wherein said constant current producing means produces alternating current so as to minimize electrolytic deposition on said probes.

5. The apparatus of claim 1 wherein said measuring means further comprises means for comparing the voltage potential of said first controlling probe with the potential of said reference probe and means for comparing the voltage potential of said second controlling probe with the potential of said reference probe.

6. The apparatus of claim 5 wherein both of said comparing means are electronic comparators and wherein the refrigeration system is operated in accordance with the output signals of the two comparators.

7. An apparatus for use as part of an ice bank control system requiring a plurality of electrodes for sensing the presence of ice around cooling coils, comprising:

a plurality of electrodes, said plurality of electrodes comprising a first sensing electrode, a second sensing electrode, a ground electrode and a reference electrode;

a mounting means for mounting said first and second sensing electrodes, said reference electrode and said ground electrode relative to one another and relative to said cooling coils, one of said sensing electrodes being farther from said cooling coils than the other of said sensing electrodes, and said ground electrode and said reference electrode being farther from said cooling coils than both said first sensing electrode and said second sensing electrode.

8. The apparatus of claim 7 wherein said electrodes are mounted to said cooling coils by said mounting means.

9. The apparatus of claim 8 wherein said mounting means comprises means for adjusting the distance between said electrodes and said cooling coils.

10. The apparatus of claim 7 wherein said mounting means further comprises a member mounted to said cooling coils, said member defining a slot therein, and a cartridge slidably received within the slot of said member.

11. The apparatus of claim 10 wherein said adjusting means comprises an adjustment member moveably connected to said first member for releasably engaging a series of ridges formed with said cartridge, thereby selectively preventing the slidable movement of said cartridge relative to said mounting means.

12. The apparatus of claim 10 wherein said plurality of electrodes comprises two sensing electrodes, a reference electrode, and a ground electrode, said electrodes being mounted on said cartridge in a manner such that the distal end of one of said sensing electrodes extends farther than the distal end of said other sensing electrode and the distal ends of said reference and ground electrodes extend farther than the distal ends of either of said sensing electrodes.

13. The apparatus of claim 1, further comprising means housing an electronic circuit mounted on a printed circuit board and for connecting cables to said circuit, said housing and connecting means comprising:

a circuit board housing having a top and four sides and being open at the bottom;

means mounting said printed circuit board within said circuit board within said circuit board housing;

a plurality of flat pin conductors attached to terminals of said printed circuit board;

a terminal housing closing the opening in the bottom of said circuit board housing by inserting therein so that said terminal housing is overlapped by the walls of said circuit board housing and comprising a base plate and an upper portion, the latter having a plurality of slots which engage said flat pin conductors and a plurality of openings for receiving electrical cables; and means for electrically connecting cables to said flat pin conductors within said terminal housing.

14. The apparatus of claim 13 wherein said terminal housing further comprises two ridges within said terminal housing on the base plate and upper portion, respectively, oriented transversely to the longitudinal axis of a received electrical cable for bending electrical cables received through said openings into an S-shape.

15. The apparatus of claim 13 wherein said means for electrically connecting said flat pin conductors to cables further comprises:

a plurality of screw-type terminals within said terminal housing; and a plurality of ribbon-type conductors mounted within said slots and electrically connected to said screw-type terminals, said ribbon-type conductors being of an arcuate shape which is straightened when said flat pin conductors are inserted into said slots so as to increase the surface area of contact between said flat pin conductor and said ribbon-type conductors and exert a holding force on said flat pin conductor.

16. The apparatus of claim 13 wherein said circuit board housing further comprises a lens mounted on the top of said circuit board housing for transmitting light emitted by a lamp mounted on a printed circuit board.

17. The apparatus of claim 13 wherein said terminal housing comprises an upper portion and a base plate held together by a plurality of screws.

18. The apparatus of claim 17 further comprising a screw insertable through a hole in the top of said circuit board housing and threadably engaging a hole in the top of said upper portion of said terminal housing so as to hold said terminal housing within said circuit board housing.

* * * * *